(12) United States Patent
Zhan et al.

(10) Patent No.: US 12,102,471 B2
(45) Date of Patent: Oct. 1, 2024

(54) ITERATIVE METHOD FOR MATERIAL DECOMPOSITION CALIBRATION IN A FULL SIZE PHOTON COUNTING COMPUTED TOMOGRAPHY SYSTEM

(71) Applicant: CANON MEDICAL SYSTEMS CORPORATION, Tochigi (JP)

(72) Inventors: Xiaohui Zhan, Vernon Hills, IL (US); Xiaofeng Niu, Vernon Hills, IL (US); Ruoqiao Zhang, Vernon Hills, IL (US)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 285 days.

(21) Appl. No.: 17/720,977

(22) Filed: Apr. 14, 2022

(65) Prior Publication Data

US 2023/0329665 A1   Oct. 19, 2023

(51) Int. Cl.
*A61B 6/58* (2024.01)
*A61B 6/03* (2006.01)
*A61B 6/42* (2024.01)
*G01T 7/00* (2006.01)
(Continued)

(52) U.S. Cl.
CPC .............. *A61B 6/585* (2013.01); *A61B 6/032* (2013.01); *A61B 6/4241* (2013.01); *G01T 7/005* (2013.01); *G06T 7/0012* (2013.01); *G06T 11/005* (2013.01); *G06T 2207/10081* (2013.01);
(Continued)

(58) Field of Classification Search
CPC ....... A61B 6/585; A61B 6/032; A61B 6/4241; A61B 6/482; G01T 7/005; G01T 1/171; G06T 7/0012; G06T 11/005; G06T 2207/10081; G06T 2207/30004; G06T 2207/30168
See application file for complete search history.

(56) References Cited

U.S. PATENT DOCUMENTS

| | | |
|---|---|---|
| 10,679,385 B1 | 6/2020 | Yanoff et al. |
| 11,166,683 B2 | 11/2021 | Carbonne Dit Leychert Garenne et al. |
| 11,249,035 B2 | 2/2022 | Zhan et al. |

(Continued)

OTHER PUBLICATIONS

Kim et al., "Feasibility Study of an Improved Single-Energy Material Decomposition Method for Computed Tomography", IEEE Transactions on Nuclear Science, vol. 69, No. 6, pp. 1366-1374. (Year: 2022).*

(Continued)

*Primary Examiner* — Kiho Kim
(74) *Attorney, Agent, or Firm* — Oblon, McClelland, Maier & Neustadt, L.L.P.

(57) ABSTRACT

A photon counting computed tomography (CT) method including receiving a first forward model including a set of first parameters and a set of second parameters corresponding to a plurality of materials and path lengths by scanning a slab at plural tube voltages and plural tube currents of an X-ray tube; evaluating an image quality of a material decomposition image reconstructed by the set of first parameters and the set of second parameters; and updating at least one second parameters from the set of second parameters if the image quality of the material decomposition image does not satisfy a predetermined threshold, wherein the updating is achieved by updating the at least one second parameter from the set of second parameters to an energy dependent parameter from a constant value.

19 Claims, 4 Drawing Sheets

(51) Int. Cl.
*G06T 7/00* (2017.01)
*G06T 11/00* (2006.01)
(52) U.S. Cl.
CPC .............. *G06T 2207/30004* (2013.01); *G06T 2207/30168* (2013.01)

(56) References Cited

U.S. PATENT DOCUMENTS

2017/0100085 A1* 4/2017 Roessl .................. A61B 6/482
2018/0078233 A1* 3/2018 Jin ........................ G06T 11/005

OTHER PUBLICATIONS

Persson et al., "AFramework for Evaluating Threshold Variation Compensation Methods in Photon Counting Spectral CT", IEEE TransactionsonMedicalImaging,vol. 31,No. 10, pp. 1861-1874. (Year: 2012).*

Sidky et al., "A Robust Method of X-Ray Source Spectrum Estimation from Transmission Measurements: Demonstrated on Computer Simulated, Scatter-Free Transmission Data", Journal of Applied Physics 97(12), 124701 (2005).

Duan et al., "CT Scanner X-Ray Spectrum Estimation from Transmission Measurements", Medical Physics 38(2), Feb. 2011.

Dickmann et al., "A Count Rate-Dependent Method for Spectral Distortion Correction in Photon Counting CT", Proc. SPIE 10573, Medical Imaging 2018: Physics of Medical Imaging, 1057311 (Mar. 9, 2018).

* cited by examiner

ITERATIVE METHOD FOR MATERIAL DECOMPOSITION CALIBRATION IN A FULL SIZE PHOTON COUNTING COMPUTED TOMOGRAPHY SYSTEM

FIELD OF THE INVENTION

The disclosure relates to material decomposition in a photon counting computed tomography system.

DESCRIPTION OF THE RELATED ART

Computed tomography (CT) systems and methods are typically used for medical imaging and diagnosis. CT systems generally create projection images through a subject's body at a series of projection angles. A radiation source, such as an X-ray tube, irradiates the body of a subject and projection images are generated at different angles. Images of the subject's body can be reconstructed from the projection images.

Conventionally, energy-integrating detectors (EIDs) and/or photon-counting detectors (PCDs) have been used to measure CT projection data. PCDs offer many advantages including their capacity for performing spectral CT, wherein the PCDs resolve the counts of incident X-rays into spectral components referred to as energy bins, such that collectively the energy bins span the energy spectrum of the X-ray beam. Unlike non-spectral CT, spectral CT generates information due to different materials exhibiting different X-ray attenuation as a function of the X-ray energy. These differences enable a decomposition of the spectrally resolved projection data into different material components, for example, the two material components of the material decomposition can be bone and water.

Even though PCDs have fast response times, at high X-ray flux rates indicative of clinical X-ray imaging, multiple X-ray detection events on a single detector may occur within the detector's time response, a phenomenon called pileup. Left uncorrected, pileup effect distorts the PCD energy response and can degrade reconstructed images from PCDs. When these effects are corrected, spectral CT has many advantages over conventional CT. Many clinical applications can benefit from spectral CT technology, including improved material differentiation since spectral CT extracts complete tissue characterization information from an imaged object.

One challenge for more effectively using semiconductor-based PCDs for spectral CT is performing the material decomposition of the projection data in a robust and efficient manner. For example, correction of pileup in the detection process can be imperfect, and these imperfections degrade the material components resulting from the material decomposition.

In a photon counting CT system, the semiconductor-based detector using direct conversion is designed to resolve the energy of the individual incoming photons and generate measurement of multiple energy bin counts for each integration period. However, due to the detection physics in such semiconductor materials (e.g. CdTe/CZT), the detector energy response is largely degraded/distorted by charge sharing, k-escape, and scattering effects in the energy deposition and charge induction process, as well as electronic noise in the associated front-end electronics. Due to finite signal induction time, at high count-rate conditions, pulse pile-up also distorts the energy response, as discussed above.

Due to sensor material non-uniformity and complexity of the integrated detection system, it is impossible to do accurate modeling of such detector response for a PCD just based on physics theories or Monte Carlo simulations with a certain modeling of the signal induction process, which modeling determines the accuracy of the forward model of each measurement. Also, due to uncertainties in the incident X-ray tube spectrum modeling, the modelling introduces additional errors in the forward model, and all these factors eventually degrade the material decomposition accuracy from the PCD measurements, therefore the generated spectral images.

Calibration methods have been proposed to solve similar problems in literature. The general idea is to use multiple transmission measurements of various known path lengths to modify the forward model such that it agrees with the calibration measurements. Some ideas are applied on estimation of the X-ray spectrum in conventional CT, see Sidky et al., Journal of Applied Physics 97(12), 124701 (2005) and Duan et al., Medical Physics 38(2), February 2011, and later adopted on photon-counting detectors to estimate the combined system spectral response, see Dickmann et al., Proc. SPIE 10573, Medical Imaging 2018: Physics of Medical Imaging, 1057311 (Mar. 9, 2018). However, there can be many variations in the detail design and implementation of the calibration method, especially considering the application feasibility in a full 3rd generation CT geometry, which has not been demonstrated or documented in literature so far.

SUMMARY

The embodiments presented herein relate to an apparatus for an iterative calibration method for the PCD forward model for material decomposition. The method initially consists of two parts: 1) an estimation of a first set of parameters (e.g., a flux independent weighted bin response function $S_{wb}(E)$ using the expectation maximization (EM) method), and 2) an estimation of a second set of parameters (e.g., a pileup correction term $P_b(E, N_b, N_{tot})$). Once the first set of parameters (e.g., $S_{wb}(E)$) is estimated from the calibration at plural tube voltage (kVp) settings for each detector pixel, it is saved as a calibration table in the system. It is then used as an input to estimate a second set of parameters (e.g., pileup correction terms $P_b(E, N_b, N_{tot})$) at higher flux scans. Both tables are then compared to a calibration phantom at plural currents (mA). If the uniformity and accuracy satisfy predetermined metrics, then the data is saved and calibration is complete. If the uniformity and accuracy does not satisfy the predetermined metrics, then a new parameter from the second set of parameters (e.g., a pileup correction term $P_b$) is calculated in the low current (mA) scans (e.g., by setting the count rate related terms in $P_b$ to zero). A pseudo pileup-free low flux data is then calculated using the flux independent weighted bin response function $S_{wb}(E)$ and the $P'_b$ and that is used to calculate a new $S_{wb}$. Each new $S_{wb}$ feeds back into the method until the uniformity and accuracy requirements are satisfied at each mA.

BRIEF DESCRIPTION OF THE DRAWINGS

The application will be better understood in light of the description which is given in a non-limiting manner, accompanied by the attached drawings in which.

DETAILED DESCRIPTION OF THE PREFERRED EMBODIMENTS

Reference throughout this specification to "one embodiment" or "an embodiment" means that a particular feature, structure, material, or characteristic described in connection with the embodiment is included in at least one embodiment of the application, but do not denote that they are present in every embodiment.

Thus, the appearances of the phrases "in one embodiment" or "in an embodiment" in various places throughout this specification are not necessarily referring to the same embodiment of the application. Furthermore, the particular features, structures, materials, or characteristics may be combined in any suitable manner in one or more embodiments.

Figure 1:
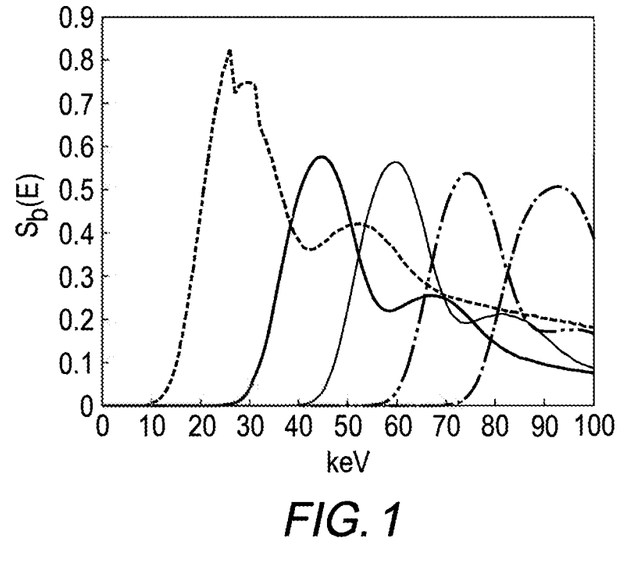
FIG. 1 shows an example of a PCD bin response function $S_b(E)$ for a photon counting detector. Each curve stands for an example function for each energy bin.

In a transmission measurement using a photon counting energy-resolving detector (PCD), the forward model can be formulated as below:

$$N_b(l_1,\ldots,l_M) = N_0 \times \int dE\, w(E) S_b(E) \exp(-\Sigma \mu_m l_m), \quad (1)$$

where $S_b(E)$ denotes the bin response function defined as $S_b(E) = \int_{E_{bL}}^{E_{bH}} R(E, E') dE'$ where $R(E,E')$ is the detector response function, and $E_{bL}$ and $E_{bH}$ are the low and high energy threshold of each counting bin. FIG. 1 shows an example model of a typical $S_b(E)$ function for a PCD, where a long tail above the energy window is induced by charge sharing, k-escape and scattering effect. The low energy tail is mostly due to the finite energy resolution from the associated electronic noise. $N_0$ is the total flux from an air scan, $\mu_m$ and $l_m$ are the $m^{th}$ basis material linear attenuation coefficient and path length. $w(E)$ is the normalized incident X-ray spectrum. In practice, both $w(E)$ and $S_b(E)$ are not exactly known, and they can be combined as one term, $S_{wb}(E) = w(E) S_b(E)$, called thereafter the weighted bin response function. If $S_{wb}(E)$ can be calibrated through measurements, the decomposition problem at low flux condition can be well solved.

For a high flux scan condition (e.g., a few percent of pulse pileup), pulse pileup introduces additional spectral distortion in the measurement. One way to correct for the pileup effect is to introduce additional correction terms (e.g. see Dickmann above, who uses the measured count rate(s) as input). And this type of additional calibration is based on an accurate estimation of the flux independent weighted bin response $S_{wb}(E)$. This leads to the first two steps in the scheme using the following forward model:

$$N_b(l_1,\ldots,l_M) = N_0 \int dE\, S_{wb}(E) * P_b(E, N_b, N_{tot}) \exp(-\Sigma \mu_m l_m)$$

The concept of this two-step calibration method requires that the low flux response term $S_{wb}$ is flux independent. In a typical CT system, the minimum flux produced by the X-ray tube sometimes is still not low enough to meet the "pileup-free" requirement for estimation of $S_{wb}$. Especially, with the usage of bowtie filters, the center detector pixels will experience much higher flux exposure with air or thin path lengths compared to the peripheral pixels. With inaccurate $S_{wb}$, it becomes more difficult to estimate the pileup term $P_b$ with high flux measurements, and introduces potential inconsistency of the calibration results across the detector channels, and at different flux conditions. Therefore, how to compensate the non-ideal measurements due to the system flux limit and improve the estimation of $S_{wb}$, then improve the overall calibration quality and stability, is what we try to solve in this proposal.

In one non-limiting embodiment, an improved calibration builds upon the two-step calibration method for the PCD forward model for material decomposition. The method consists of two parts: 1) estimation of the flux independent weighted bin response function $S_{wb}(E)$ using the expectation maximization (EM) method, and 2) estimation of the pileup correction term $P_b(E, N_b, N_{tot})$ which is a function of energy (E) and the measured bin counts ($N_b$, $N_{tot}$), where $N_b$ is the individual bin count and $N_{tot}$ is the total count of all the energy bins. The calibrated forward model can be expressed as:

$$N_b(l_1,\ldots,l_M) = N_0 \int^{E_{max}} dE\, S_{wb}(E) * P_b(E, N_b, N_{tot}) \exp(-\Sigma \mu_m l_m) \quad (2)$$

Plural different materials (e.g., 2-5 different materials such as polypropylene, water, aluminium, titanium/copper, and k-edge materials) can be used to calibrate the weighted bin response function $S_{wb}(E)$ at low flux. With more selective materials used in the calibration, the number of total path lengths is reduced to achieve equivalent or better results.

Step 1: With an appropriate tube spectrum modelling to capture the characteristic peaks in the incident spectrum, and a physical model to simulate the photon-counting detector spectral response, an initial guess of $S_{wb}(E)$ can be produced. By using the EM method (e.g., see Sidky et al.), $S_{wb}(E)$ can be reliably estimated for this very ill-conditioned problem based on a few transmission measurements.

Here, $P_b(E, N_b, N_{tot})$ is assumed to be constant in Step 1. The calibrated forward model can be simplified to a system of linear equations $$N_b(l_1,\ldots,l_M) = N_0 \int^{E_{max}} dE\, S_{wb}(E) \exp(-\Sigma \mu_m l_m) \quad (3)$$

Usually, the number of data measurements (M) is much smaller than the number of unknowns ($E_{max}$). With the assumption of Poisson distribution of the data acquisition, an iterative EM algorithm can be derived to find the optimal estimation of the unknown energy bin response function $S_{wb}(E)$, as described below.

When estimating the bin response function using low flux data acquisition, the pileup effect correction $P_b$ is assumed to be a known term (e.g., constant). So, the model is simplified to $$N_b = N_0 \int dE\, S_{wb}(E)[\exp[-\Sigma \mu_m(E) l_m]] \quad (4)$$

Let $A^j(E) = \exp[-\Sigma \mu_m(E) l_m^j]$ represent the attenuated pathlength for j-th measurement. Thus, for each measurement j, we have $$N_b^j = N_0 \int dE\, S_{wb}(E) A^j(E) = N_0 \Sigma_E S_{wb}(E) A^j(E) \quad (5)$$

With M measurements, the data acquisition can be written in the matrix form below $$N_0 \begin{pmatrix} A^1(1) & \cdots & A^1(E_{max}) \\ \vdots & \ddots & \vdots \\ A^M(1) & \cdots & A^M(E_{max}) \end{pmatrix}_{M \times E_{max}} \cdot \begin{pmatrix} S_{wb}(1) \\ \vdots \\ S_{wb}(E_{max}) \end{pmatrix}_{E_{max} \times 1} = \begin{pmatrix} N_b^1 \\ \vdots \\ N_b^M \end{pmatrix}_{M \times 1}$$

or $A \cdot S_{wb} = N_b$

By applying the EM iterative algorithm, the $S_{wb}$ can be estimated by $$S_{wb}^{(k+1)} = S_{wb}^{(k)} \odot ((A^T \cdot (N_b \oslash (A \cdot S_{wb}^{(k)}))) \oslash (A^T \cdot 1)) \quad (6)$$

where
k: iteration number
·: matrix multiplication
⊙: element-wise multiplication
⊘: element-wise division
1: vector of ones with size of M×1
the updating formula for $S_{wb}(E)$ is given by $$S_{wb}^{(k+1)}(E) = S_{wb}^{(k)}(E) \frac{\Sigma_{j'} A^{j'}(E) \frac{N_b^{j'}}{\Sigma_{E'} A^{j'}(E') s_{wb}^{(k)}(E')}}{\Sigma_{j'} A^{j'}(E)} \quad (7)$$

Step 2: Once $S_{wb}(E)$ is estimated from the calibration at each tube voltage (kVp) setting for each detector pixel, it is saved as a calibration table (e.g., in hardware or software) within the system. It will be used as an input to further estimate the pileup correction terms $P_b(E, N_b, N_{tot})$ at higher flux scans. Both tables are then used for the material decomposition in object/patient scans to estimate the basis material path lengths.

The calibration tables are updated from time to time based on the system/detector performance variations. To further improve the calibration quality at high flux condition, an iterative calibration method is proposed based on the two-step calibration framework, by improving the estimation accuracy of the low flux response function $S_{wb}$ and achieve better overall estimation accuracy at higher flux as well.

Figure 2:
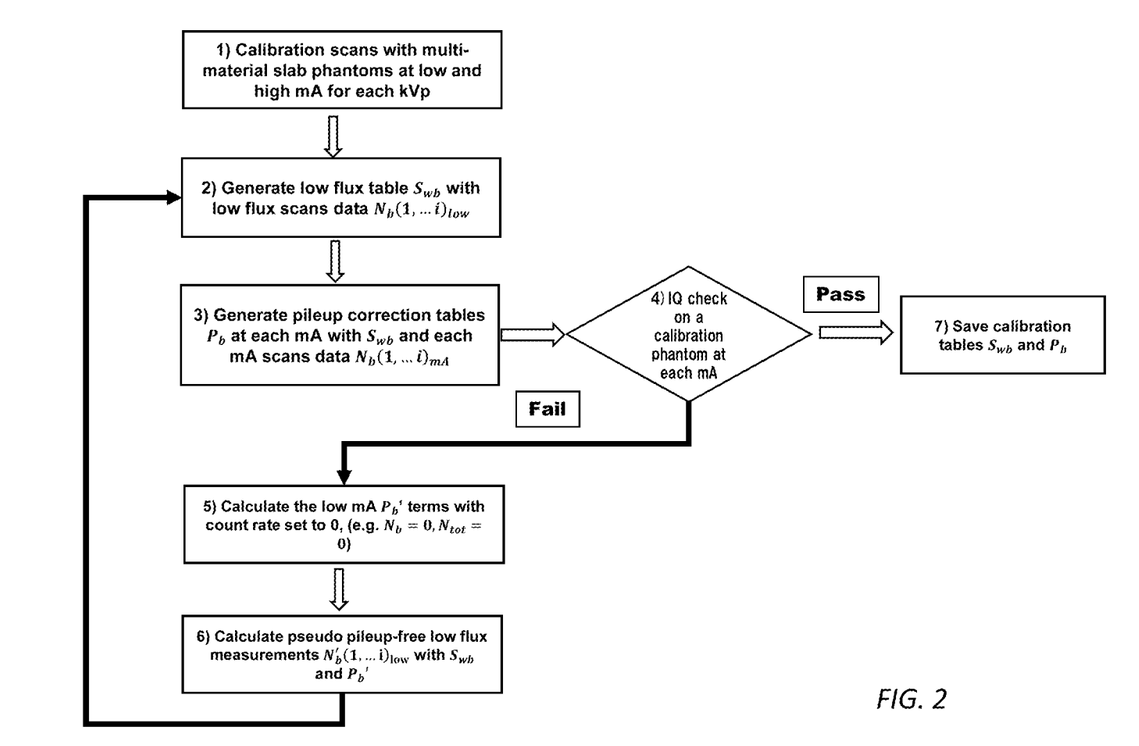
FIG. 2 shows an iterative material decomposition calibration and processing workflow.

The high-level workflow of the above process is demonstrated in FIG. 2. Steps 1) to 4) represent the calibration workflow, steps 5) to 8) demonstrate how the calibration tables are updated in an iterative process, and step 9) represents the output of the completed calibration tables used in the operational scans of patients/objects to produce spectral images.

First, Step 1), a series of low and high flux scans on rectangular slabs of different uniform known materials are collected in a photon counting CT system using stationary configuration at each tube kVp setting, which is the peak potential applied on the X-ray tube. Typical CT systems support a few kVp settings from 70 to 140 kVp which generate different energy spectrums from the X-ray tube for different scan protocol. For a CT scan, both mA and kVp need to be pre-selected before the tube is turned on. The photon counting detector generates b bins of counts $N_b$ with pre-set energy thresholds for each of the slabs i. Then, Step 2), the low flux calibration data $N_b(1, \ldots, i)_{low}$ is used to estimate a set of first parameters, the low flux response term $S_{wb}$ at each kVp setting for each detector pixel. Step 3), the low and high calibration data $N_b(1, \ldots, i)_{mA}$ is used to estimate a set of second parameters, the pileup term $P_b$ at each mA, including the low mA scans. Step 4), with the estimation calibration tables of $S_{wb}$, the set of first parameters, and $P_b$, the set of second parameters, for each detector pixel, the quality of the calibration is checked on a quality phantom (e.g., a uniform water phantom, or phantom with multiple inserts with uniform known materials). Step 5), the image quality is assessed with predefined standards (e.g., HU at different ROIs, +/−5HU), and if it is passed, the current calibration tables are saved and then used for the following patient/object scans data processing. Otherwise, the procedure goes through the next pass of calibration analysis. Step 6), the second parameters in the set of second parameters is updated by setting the energy dependent parameter of one of the second parameters from the set of second parameters to a constant value. So the pileup reversing term $P'_b$, the updated second parameter from the set of second parameters, in the low mA scans is calculated by setting the count rate related terms to 0 in $P_b$ (e.g., $P_b(E, N_b, N_{tot})$, one will set $N_b$ and $N_{tot}$ to be ( ) with previously estimated parameters in $P_b$ at that low mA). Then, Step 7) the pseudo pileup-free low flux data $N'_b(1, \ldots, i)_{low}$ is calculated based on the previous pass $S_{wb}$ and $P'_b$. Step 8), $N'_b(1, \ldots, i)_{low}$ is then used to estimate the next pass of $S_{wb}$. The process is repeated from the second step until the quality check passes for all the mA scans covered by the calibration. Step 9), these calibration tables are saved to be used in the operational scans of patients/objects to produce spectral images. Here, commonly examined standards are: image CT number accuracy, uniformity, spatial resolution, noise and artifacts. To check the quality of this calibration, these metrics should all be checked, especially the accuracy and artifacts like ring or bands in the image, which indicate the calibration is not good enough.

Figure 3:
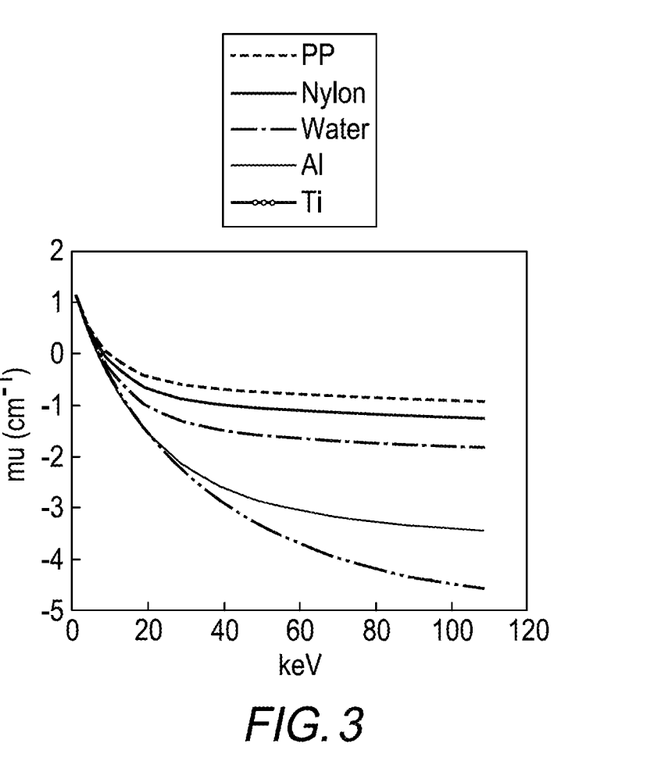
FIG. 3 shows normalized linear attenuation coefficients for different materials.

To choose the optimal materials and path lengths for this calibration, one can use the normalized linear attenuation coefficient vs. energy curves (FIG. 3) to choose the ones that are different from each other, e.g., polypropylene, water, aluminum, and titanium. Such a group of combinations allows calibrations which covers a large range of common materials present in human body.

In order to satisfy the low flux condition through the calibration measurement to minimize the pileup effect in the flow diagram, step 1, one can select to use nτ<x, where x ~0.005-0.01 and n is the pixel count rate with the lowest tube flux setting, and τ is the effective dead time of the PCD Application Specific Integrated Circuit (ASIC). These ideal conditions are not always met with the x-ray tube used in the CT system. With bowtie filters, in the center detector region, the air and thin slab measurements can still have a significant portion (e.g. a few percent) of the pileup events that contaminate the estimation of low flux response function $S_{wb}$, by forcing it to match the data with pileup effect. Hence, it increases the difficulty of the high flux pileup correction term estimation due to the inaccurate flux-independent term $S_{wb}$. The iterative method modifies the two-step method by introducing a pileup-correction step utilizing the previous calibration results.

The calibration measurements should be taken with sufficient statistics to minimize the influence of the statistical fluctuation. One non-limiting example is to use >1000 times more statistics as the typical integration period for the calibration data sets to minimize the transferred statistical error in the calibration. Each energy bin b of the calibration measurements will be used to update the corresponding $S_{wb}(E)$ and $P_b(E, N_b, N_{tot})$.

Since one can only do limited number of measurements with a few energy bins, the estimation is very ill-conditioned. In this case, a good initial guess is crucial for an accurate estimation as it provides additional constraints for the EM method. One of the design variations to accommodate non-ideal detectors is to allow a more flexible energy window for each bin in the initial guess of $S_b$, especially with small variations in the actual energy threshold setting of the ASIC. By setting the low threshold x keV lower, and high threshold y keV higher, the initial $S_b$ becomes:

$$S_b(E) = \int_{EbL-x}^{EbH+y} R(E, E') dE' \quad (8)$$

where x, y can be chosen between 5 to 10 keV to allow certain variations in the ASIC performance, while still providing additional constraints for the EM problem.

To capture the spectrum variation across the fan beam after bowtie filter and detector response variation across different detector pixels, this calibration process is done pixel by pixel with each bowtie/filter configuration.

The design described in the present application employs more than two materials in the calibration, which provides more sensitivity to constraint the weighted bin response function estimation problem of the photon counting detectors.

In addition, the method utilizes the parameterization for the pileup correction terms $P_b$ which is a function of E, $N_b$ and $N_{tot}$. The total count term $N_{tot}$ is introduced for a better approximation of the true pileup phenomena, and can significantly improve the model capability at higher flux condition with fewer parameters.

Furthermore, various calibration path length ranges are used at different fan angles to improve the calibration accuracy and efficiency. The slab scans used for the forward model calibration can be selected based on the imaging task to generate the best image quality.

An X-ray CT will be described as an example of a medical image diagnostic modality herein. In that context, an information processing method of information acquired by imaging performed by the X-ray CT will be described.

Figure 4:
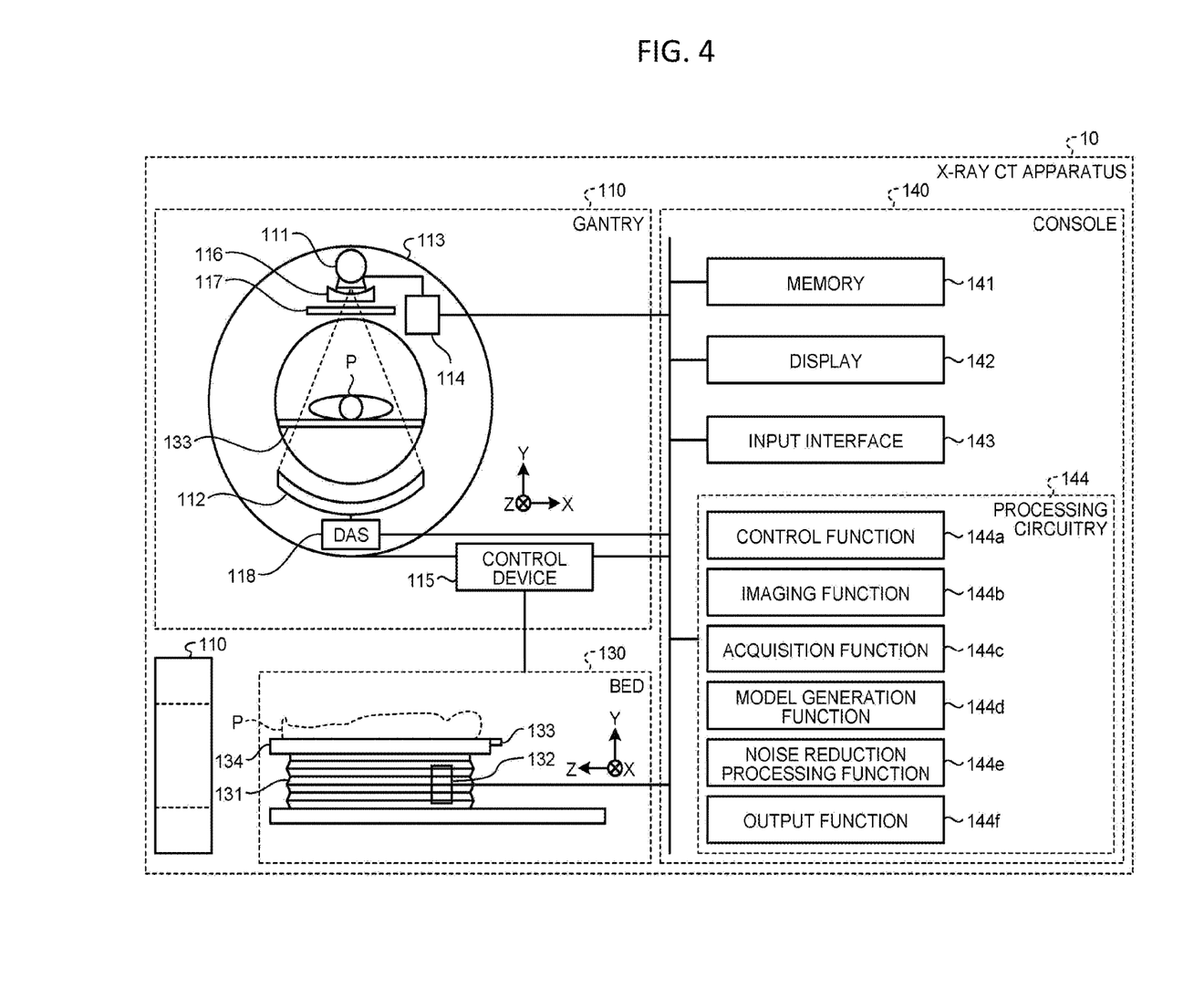
FIG. 4 is a block diagram of an exemplary configuration of an X-ray CT apparatus imaging a person as a subject according to an exemplary embodiment described below

The X-ray CT is implemented, for example, in an X-ray CT apparatus 10 illustrated in FIG. 4. FIG. 4 is a block diagram illustrating an example of a configuration of the X-ray CT apparatus 10 according to a first embodiment. For example, the X-ray CT apparatus 10 has a gantry 110, a bed 130, and a console 140.

In FIG. 4, it is assumed that the longitudinal direction of a rotating shaft of a rotating frame 113 or a tabletop 133 of the bed 130 in a non-tilted state is a Z axis direction. Furthermore, it is assumed that an axial direction orthogonal to the Z axis direction and horizontal to a floor surface is an X axis direction. Furthermore, it is assumed that an axial direction orthogonal to the Z axis direction and perpendicular to the floor surface is a Y axis direction. Note that FIG. 4 illustrates the gantry 110 drawn from a plurality of directions for convenience of description and the X-ray CT apparatus 10 has one gantry 110.

The gantry 110 includes an X-ray tube 111, an X-ray detector 112, the rotating frame 113, an X-ray high voltage device 114, a control device 115, a wedge 116, a collimator 117, and a data acquisition system (DAS) 118.

The X-ray tube 111 is a vacuum tube having a cathode (filament) that generates thermoelectrons and an anode (target) that generates X-rays in response to a collision of thermoelectrons. The X-ray tube 111 emits the thermoelectrons toward the anode from the cathode by the application of a high voltage from the X-ray high voltage device 114, thereby generating the X-rays to be emitted to a subject P.

The X-ray detector 112 detects the X-rays emitted from the X-ray tube 111 and passed through the subject P, and outputs a signal corresponding to the dose of the detected X-rays to the DAS 118. The X-ray detector 112, for example, includes a plurality of detection element arrays in which a plurality of detection elements are arranged in a channel direction (channel direction) along one arc centered on a focal point of the X-ray tube 111. The X-ray detector 112, for example, has a structure in which the detection element arrays with the detection elements arranged in the channel direction are arranged in a row direction (slice direction and row direction).

For example, the X-ray detector 112 is an indirect conversion type detector having a grid, a scintillator array, and a photosensor array. The scintillator array has a plurality of scintillators. Each of the scintillators has a scintillator crystal that outputs light with a photon quantity corresponding to an incident X-ray dose. The grid has an X-ray shielding plate that is disposed on the surface of the scintillator array on an X-ray incident side and absorbs scatted X-rays. The grid may also be referred to as a collimator (a one-dimensional collimator or a two-dimensional collimator). The photosensor array has a function of converting light into an electrical signal corresponding to the amount of light from the scintillator, and has, for example, photosensors such as photodiodes. Note that the X-ray detector 112 may be a direct conversion type detector having a semiconductor element that converts the incident X-rays into electrical signals.

The rotating frame 113 is an annular frame that supports the X-ray tube 111 and the X-ray detector 112 so as to face each other and rotates the X-ray tube 111 and the X-ray detector 112 by the control device 115. For example, the rotating frame 113 is a casting made of aluminum. Note that the rotating frame 113 can further support the X-ray high voltage device 114, the wedge 116, the collimator 117, the DAS 118 and the like, in addition to the X-ray tube 111 and the X-ray detector 112. Moreover, the rotating frame 113 can further support various configurations not illustrated in FIG. 4. Hereinafter, in the gantry 110, the rotating frame 113 and a part, which rotationally moves with the rotating frame 113, are also referred to as a rotating part.

The X-ray high voltage device 114 has electric circuitry such as a transformer and a rectifier, and has a high voltage generation device that generates a high voltage to be applied to the X-ray tube 111 and an X-ray control device that controls an output voltage corresponding to the X-rays generated by the X-ray tube 111. The high voltage generation device may be a transformer type device or an inverter type device. Note that the X-ray high voltage device 114 may be provided on the rotating frame 113, or may also be provided on a fixed frame (not illustrated).

The control device 115 has processing circuitry having a central processing unit (CPU) and the like, and a driving mechanism such as a motor and an actuator. The control device 115 receives input signals from an input interface 143 and controls the operations of the gantry 110 and the bed 130. For example, the control device 115 controls the rotation of the rotating frame 113, the tilt of the gantry 110, the operation of the bed 130, and the like. As an example, as control for tilting the gantry 110, the control device 115 rotates the rotating frame 113 around an axis parallel to the X axis direction based on information on an input inclination angle (tilt angle). Note that the control device 115 may be provided in the gantry 110 or may also be provided in the console 140.

The wedge 116 is an X-ray filter for adjusting the dose of the X-rays emitted from the X-ray tube 111. Specifically, the wedge 116 is an X-ray filter that attenuates the X-rays emitted from the X-ray tube 111 such that the X-rays emitted from the X-ray tube 111 to the subject P have a predetermined distribution. For example, the wedge 116 is a wedge filter or a bow-tie filter and is manufactured by processing aluminum and the like to have a predetermined target angle and a predetermined thickness.

The collimator 117 is a lead plate and the like for narrowing down the emission range of the X-rays having transmitted through the wedge 116 and forms a slit by a combination of a plurality of lead plates and the like. Note that the collimator 117 may also be referred to as an X-ray diaphragm. Furthermore, although FIG. 4 illustrates a case where the wedge 116 is disposed between the X-ray tube 111 and the collimator 117, the collimator 117 may be disposed between the X-ray tube 111 and the wedge 116. In such a case, the wedge 116 attenuates the X-rays, which are emitted from the X-ray tube 111 and whose emission range is limited by the collimator 117, by allowing the X-rays to pass therethrough.

The DAS 118 acquires X-ray signals detected by each detector element included in the X-ray detector 112. For example, the DAS 118 has an amplifier that performs an amplification process on electrical signals output from each detector element and an A/D converter that converts the electrical signals to digital signals, and generates detection data. The DAS 118 is implemented by, for example, a processor.

The data generated by the DAS 118 is transmitted from a transmitter having a light emitting diode (LED) provided on the rotating frame 113 to a receiver having a photodiode provided on a non-rotating part (for example, a fixed frame and the like and not illustrated in FIG. 4) of the gantry 110 by optical communication, and is transmitted to the console 140. The non-rotating part is, for example, a fixed frame and the like that rotatably supports the rotating frame 113. Note that the data transmission method from the rotating frame 113 to the non-rotating part of the gantry 110 is not limited to the optical communication, and may adopt any non-contact type data transmission method or a contact type data transmission method.

The bed 130 is a device that places and moves the subject P to be scanned and includes a pedestal 131, a couch driving device 132, the tabletop 133, and a support frame 134. The pedestal 131 is a casing that supports the support frame 134 so as to be movable in a vertical direction. The couch driving device 132 is a driving mechanism that moves the tabletop 133, on which the subject P is placed, in a long axis direction of the tabletop 133 and includes a motor, an actuator and the like. The tabletop 133 provided on the upper surface of the support frame 134 is a plate on which the subject P is placed. Note that the couch driving device 132 may also move the support frame 134 in the long axis direction of the tabletop 133 in addition to the tabletop 133.

The console 140 has a memory 141, a display 142, the input interface 143, and processing circuitry 144. Although the console 140 is described as a separate body from the gantry 110, the gantry 110 may include the console 140 or a part of each component of the console 140.

The memory 141 is implemented by, for example, a semiconductor memory element such as a random access memory (RAM) and a flash memory, a hard disk, an optical disk, and the like. For example, the memory 141 stores a computer program for circuitry included in the X-ray CT apparatus 10 to perform its functions. Furthermore, the memory 141 stores various information obtained by imaging the subject P. Note that the memory 141 may be implemented by a server group (cloud) connected to the X-ray CT apparatus 10 via a network.

The display 142 displays various information. For example, the display 142 displays an image based on the imaging described herein. Furthermore, for example, the display 142 displays a graphical user interface (GUI) for receiving various instructions, settings, and the like from a user via the input interface 143. For example, the display 142 is a liquid crystal display or a cathode ray tube (CRT) display. The display 142 may be a desktop type display, or may be composed of a tablet terminal and the like capable of wirelessly communicating with the body of the X-ray CT apparatus 10.

Although the X-ray CT apparatus 10 is described as including the display 142 in FIG. 4, the X-ray CT apparatus 10 may include a projector instead of or in addition to the display 142. Under the control of the processing circuitry 144, the projector can perform projection onto a screen, a wall, a floor, the body surface of the subject P, and the like. As an example, the projector can also perform projection onto any plane, object, space, and the like by projection mapping.

The input interface 143 receives various input operations from a user, converts the received input operations into electrical signals, and outputs the electrical signals to the processing circuitry 144. For example, the input interface 143 is implemented by a mouse, a keyboard, a trackball, a switch, a button, a joystick, a touch pad for performing an input operation by touching an operation surface, a touch screen in which a display screen and a touch pad are integrated, non-contact input circuitry using an optical sensor, voice input circuitry, and the like. Note that the input interface 143 may be composed of a tablet terminal and the like capable of wirelessly communicating with the body of the X-ray CT apparatus 10. Furthermore, the input interface 143 may be circuitry that receives an input operation from a user by motion capture. As an example, the input interface 143 can receive a user's body movement, line of sight, and the like as an input operation by processing a signal acquired via a tracker or an image collected for a user. Furthermore, the input interface 143 is not limited to one including physical operation parts such as a mouse and a keyboard. For example, an example of the input interface 143 includes electric signal processing circuitry which receives an electric signal corresponding to an input operation from an external input device separately provided from the X-ray CT apparatus 10 and outputs the electric signal to the processing circuitry 144.

The processing circuitry 144 controls the overall operation of the X-ray CT apparatus 10 by performing a control function 144a, an imaging function 144b, an acquisition function 144c, a model generation function 144d, a noise reduction processing function 144e, and an output function 144f.

For example, the processing circuitry 144 reads a computer program corresponding to the control function 144a from the memory 141 and executes the read computer program, thereby controlling various functions, such as the imaging function 144b, the acquisition function 144c, the model generation function 144d, the noise reduction processing function 144e, and the output function 144f, based on various input operations received from a user via the input interface 143.

Furthermore, for example, the processing circuitry 144 reads a computer program corresponding to the imaging function 144b from the memory 141 and executes the read computer program, thereby imaging the subject P. For example, the imaging function 144b controls the X-ray high voltage device 114 to supply the X-ray tube 111 with a high voltage. With this, the X-ray tube 111 generates X-rays to be emitted to the subject P. Furthermore, the imaging function 144b controls the couch driving device 132 to move the subject P into an imaging port of the gantry 110. Furthermore, the imaging function 144b adjusts the position of the wedge 116 and the opening degree and position of the collimator 117, thereby controlling the distribution of the X-rays emitted to the subject P. Furthermore, the imaging function 144b controls the control device 115 to rotate the rotating part. Furthermore, while the imaging is performed by the imaging function 144b, the DAS 118 acquires X-ray signals from the respective detection elements in the X-ray detector 112 and generates detection data.

Furthermore, the imaging function 144*b* performs pre-processing on the detection data output from the DAS 118. For example, the imaging function 144*b* performs pre-processing, such as logarithmic transformation processing, offset correction processing, inter-channel sensitivity correction processing, and beam hardening correction, on the detection data output from the DAS 118. Note that the data subjected to the pre-processing is also described as raw data. Furthermore, the detection data before the pre-processing and the raw data subjected to the pre-processing are also collectively described as projection data.

Furthermore, for example, the processing circuitry 144 reads a computer program corresponding to the acquisition function 144*c* from the memory 141 and executes the read computer program to acquire image data. Furthermore, for example, the processing circuitry 144 reads a computer program corresponding to the model generation function 144*d* from the memory 141 and executes the read computer program, thereby creating and/or using the energy dependent forward model. Furthermore, for example, the processing circuitry 144 reads a computer program corresponding to the noise reduction processing function 144*e* from the memory 141 and executes the read computer program, thereby reducing noise in input subject data to obtain denoised data. Furthermore, for example, the processing circuitry 144 reads a computer program corresponding to the output function 144*f* from the memory 141 and executes the read computer program, thereby outputting an image based on the denoised data.

In the X-ray CT apparatus 10 illustrated in FIG. 4, the respective processing functions are stored in the memory 141 in the form of the computer programs executable by a computer. The processing circuitry 144 is a processor that performs a function corresponding to each computer program by reading and executing the computer program from the memory 141. In other words, the processing circuitry 144 having read the computer program has a function corresponding to the read computer program.

Note that, in FIG. 4, it has been described that the control function 144*a*, the imaging function 144*b*, the acquisition function 144*c*, the model generation function 144*d*, the noise reduction processing function 144*e*, and the output function 144*f* are implemented by the single processing circuitry 144, but the processing circuitry 144 may be configured by combining a plurality of independent processors, and each processor may be configured to perform each function by executing each computer program. Furthermore, each processing function of the processing circuitry 144 may be performed by being appropriately distributed or integrated into a single circuit or a plurality of processing circuits.

Furthermore, the processing circuitry 144 may also perform the functions by using a processor of an external device connected via the network. For example, the processing circuitry 144 reads and executes the computer program corresponding to each function from the memory 141 and uses, as computation resources, a server group (cloud) connected to the X-ray CT apparatus 10 via the network, thereby performing each function illustrated in FIG. 4.

Furthermore, although FIG. 4 illustrates only the single memory 141, the X-ray CT apparatus 10 may include a plurality of physically separated memories. For example, the X-ray CT apparatus 10 may separately include, as the memory 141, a memory that stores a computer program required when circuitry included in the X-ray CT apparatus 10 performs its function, a memory that stores various information obtained by imaging the subject P, and a memory that stores the model described herein.

Additional embodiments are set forth in the listing of parentheticals listed below.

(1) A photon counting computed tomography (PCCT) apparatus including, but not limited to, processing circuitry configured to: receive a first forward model including a set of first parameters and a set of second parameters corresponding to a plurality of materials and path lengths by scanning a slab at plural tube voltages and plural tube currents of an X-ray tube, evaluate an image quality of a material decomposition image reconstructed by the set of first parameters and the set of second parameters, and update at least one second parameters from the set of second parameters if the image quality of the material decomposition image does not satisfy a predetermined threshold, wherein the update of the at least one second parameter from the set of second parameters is achieved by updating the at least one second parameter from the set of second parameters to an energy dependent parameter from a constant value.

(2) The PCCT apparatus according to (1), wherein the at least one second parameter from the set of second parameters corresponds to a low tube current condition which is less influenced by pile-up than the at least one second parameter before being updated.

(3) The PCCT apparatus according to either of (1) and (2), wherein the processing circuitry is further configured to update remaining second parameters from the set of second parameters corresponding to higher tube current based on the at least one second parameter from the set of second parameters corresponding to low tube current.

(4) The PCCT apparatus according to any one of (1)-(3), wherein the processing circuitry is further configured to update the forward model based on the updated at least one second parameter.

(5) The PCCT apparatus according to (4), wherein the processing circuitry is further configured to evaluate an image quality of the material decomposition image reconstructed based on the updated forward model.

(6) The PCCT apparatus according to any one of (1)-(5), wherein the processing circuitry configured to evaluate the image quality of the material decomposition image reconstructed by the set of first parameters and the set of second parameters comprises processing circuitry configured to perform a pixel by pixel evaluation.

(7) The PCCT apparatus according to any one of (1)-(6), wherein the set of second parameters are related to pileup correction.

(8) The PCCT apparatus according to any one of (1)-(7), wherein the set of first parameters depend on a bin response function.

(9) The PCCT apparatus according to any one of (1)-(8), wherein the processing circuitry configured to receive the first forward model comprises processing circuitry configured to scan a plurality of slabs at the plural tube voltages and the plural tube currents of an X-ray tube.

(10) The PCCT apparatus according to any one of (1)-(9), wherein the energy dependent parameter updated from a constant value is updated by setting all count rate terms to zero.

(11) A photon counting computed tomography (CT) method, including, but not limited to: receiving a first forward model including a set of first parameters and a set of second parameters corresponding to a plurality of materials and path lengths by scanning a slab at plural tube voltages and plural tube currents of an X-ray tube;

evaluating an image quality of a material decomposition image reconstructed by the set of first parameters and the set of second parameters; and updating at least one second parameters from the set of second parameters if the image quality of the material decomposition image does not satisfy a predetermined threshold, wherein the update of the at least one second parameter from the set of second parameters is achieved by updating the at least one second parameter from the set of second parameters to an energy dependent parameter from a constant value.

(12) The method according to (11), wherein the at least one second parameter from the set of second parameters corresponds to a low tube current condition which is less influenced by pile-up than the at least one second parameter before being updated.

(13) The method according to either of (11) and (12), further comprising updating remaining second parameters from the set of second parameters corresponding to higher tube current based on the at least one second parameter from the set of second parameters corresponding to low tube current.

(14) The method according to any one of (11)-(13), further comprising updating the forward model based on the updated at least one second parameter.

(15) The method according to (14), further comprising evaluating an image quality of the material decomposition image reconstructed based on the updated forward model.

(16) The method according to any one of (11)-(15), evaluating the image quality of the material decomposition image reconstructed by the set of first parameters and the set of second parameters comprises performing a pixel by pixel evaluation.

(17) The method according to any one of (11)-(16), wherein the set of second parameters are related to pileup correction.

(18) The method according to any one of (11)-(17), wherein the set of first parameters depend on a bin response function.

(19) The method according to any one of (11)-(18), wherein receiving the first forward model includes, but is not limited to, scanning a plurality of slabs at the plural tube voltages and the plural tube currents of an X-ray tube.

(20) The method according to any one of (11)-(19), wherein the energy dependent parameter updated from a constant value is updated by setting all count rate terms to zero.

(21) A non-transitory computer-readable storage medium storing computer-readable instructions that, when executed by a computer, cause the computer to perform a method according to any one of (11)-(20).

Numerous modifications and variations of the embodiments presented herein are possible in light of the above teachings. It is therefore to be understood that within the scope of the claims, the disclosure may be practiced otherwise than as specifically described herein.

The invention claimed is:

1. A photon counting computed tomography (CT) apparatus, comprising:
processing circuitry configured to:
receive a first forward model including a set of first parameters and a set of second parameters corresponding to a plurality of materials and path lengths by scanning a slab at plural tube voltages and plural tube currents of an X-ray tube,
evaluate an image quality of a material decomposition image reconstructed by the set of first parameters and the set of second parameters, and
update at least one second parameter from the set of second parameters if the image quality of the material decomposition image does not satisfy a predetermined threshold, wherein the updating of the at least one second parameter from the set of second parameters is achieved by updating the at least one second parameter from the set of second parameters to an energy dependent parameter from a constant value.

2. The photon counting computed tomography (CT) apparatus according to claim 1, wherein the at least one second parameter from the set of second parameters corresponds to a low tube current condition which is less influenced by pile-up than the at least one second parameter before being updated.

3. The photon counting computed tomography (CT) apparatus according to claim 2, wherein the processing circuitry is further configured to update remaining second parameters from the set of second parameters corresponding to higher tube current based on the at least one second parameter from the set of second parameters corresponding to low tube current.

4. The photon counting computed tomography (CT) apparatus according to claim 1, wherein the processing circuitry is further configured to update the forward model based on the updated at least one second parameter.

5. The photon counting computed tomography (CT) apparatus according to claim 4, wherein the processing circuitry is further configured to evaluate an image quality of the material decomposition image reconstructed based on the updated forward model.

6. The photon counting computed tomography (CT) apparatus according to claim 1, wherein the processing circuitry configured to evaluate the image quality of the material decomposition image reconstructed by the set of first parameters and the set of second parameters comprises processing circuitry configured to perform a pixel-by-pixel evaluation.

7. The photon counting computed tomography (CT) apparatus according to claim 1, wherein the set of second parameters are related to pileup correction.

8. The photon counting computed tomography (CT) apparatus according to claim 1, wherein the set of first parameters depend on a bin response function.

9. The photon counting computed tomography (CT) apparatus according to claim 1, wherein the processing circuitry configured to receive the first forward model comprises processing circuitry configured to scan a plurality of slabs at the plural tube voltages and the plural tube currents of the X-ray tube.

10. The photon counting computed tomography (CT) apparatus according to claim 1, wherein the energy dependent parameter updated from a constant value is updated by setting all count rate terms to zero.

11. A photon counting computed tomography (CT) method, comprising:
receiving a first forward model including a set of first parameters and a set of second parameters corresponding to a plurality of materials and path lengths by scanning a slab at plural tube voltages and plural tube currents of an X-ray tube;
evaluating an image quality of a material decomposition image reconstructed by the set of first parameters and the set of second parameters; and
updating at least one second parameter from the set of second parameters if the image quality of the material decomposition image does not satisfy a predetermined threshold, wherein the updating of the at least one second parameter from the set of second parameters is achieved by updating the at least one second parameter from the set of second parameters to an energy dependent parameter from a constant value.

12. The method according to claim 11, wherein the at least one second parameter from the set of second parameters corresponds to a low tube current condition which is less influenced by pile-up than the at least one second parameter before being updated.

13. The method according to claim 12, further comprising updating remaining second parameters from the set of second parameters corresponding to higher tube current based on the at least one second parameter from the set of second parameters corresponding to low tube current.

14. The method according to claim 11, further comprising updating the forward model based on the updated at least one second parameter.

15. The method according to claim 14, further comprising evaluating an image quality of the material decomposition image reconstructed based on the updated forward model.

16. The method according to claim 11, evaluating the image quality of the material decomposition image reconstructed by the set of first parameters and the set of second parameters comprises performing a pixel-by-pixel evaluation.

17. The method according to claim 11, wherein the set of second parameters are related to pileup correction.

18. The method according to claim 11, wherein the set of first parameters depend on a bin response function.

19. A non-transitory computer-readable storage medium storing computer-readable instructions that, when executed by a computer, cause the computer to perform a method for calibrating a photon counting computed tomography (CT) apparatus, the method comprising:

receiving a first forward model including a set of first parameters and a set of second parameters corresponding to a plurality of materials and path lengths by scanning a slab at plural tube voltages and plural tube currents of an X-ray tube, evaluating an image quality of a material decomposition image reconstructed by the set of first parameters and the set of second parameters, and updating at least one second parameter from the set of second parameters if the image quality of the material decomposition image does not satisfy a predetermined threshold, wherein the updating of the at least one second parameter from the set of second parameters is achieved by updating the at least one second parameter from the set of second parameters to an energy dependent parameter from a constant value.

* * * * *